(12) United States Patent
Yoshimoto et al.

(10) Patent No.: US 9,492,842 B2
(45) Date of Patent: Nov. 15, 2016

(54) CELL CULTURE MEMBRANE, CELL CULTURE SUBSTRATE, AND METHOD FOR MANUFACTURING CELL CULTURE SUBSTRATE

(75) Inventors: Yasuo Yoshimoto, Tokyo (JP); Kentaro Kamimae, Tokyo (JP); Yuki Tanabe, Tokyo (JP); Taku Oguni, Ichihara (JP); Takashi Inoue, Ichihara (JP); Tsutomu Mochizuki, Ichihara (JP); Makoto Hirama, Ichihara (JP); Teruo Fujii, Tokyo (JP); Hiroshi Kimura, Tokyo (JP); Hideto Tozawa, Tokyo (JP)

(73) Assignees: KISCO LTD., Osaka (JP); DAISANKASEI CO., LTD., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 14/128,089
(22) PCT Filed: Jun. 22, 2012
(86) PCT No.: PCT/JP2012/066075
§ 371 (c)(1),
(2), (4) Date: Apr. 7, 2014
(87) PCT Pub. No.: WO2012/176908
PCT Pub. Date: Dec. 27, 2012

(65) Prior Publication Data
US 2014/0212974 A1 Jul. 31, 2014

(30) Foreign Application Priority Data
Jun. 24, 2011 (JP) ................. 2011-140961

(51) Int. Cl.
*B05D 1/00* (2006.01)
*C12M 1/12* (2006.01)
(Continued)

(52) U.S. Cl.
CPC ................ *B05D 1/60* (2013.01); *C12M 23/20* (2013.01); *C12M 25/02* (2013.01); *C12N 5/0068* (2013.01); *C12N 2533/30* (2013.01)

(58) Field of Classification Search
USPC ....................... 427/255.6; 435/401
See application file for complete search history.

(56) References Cited

U.S. PATENT DOCUMENTS 5,906,937 A 5/1999 Sugiyama et al.

2003/0012956 A1 1/2003 Nakamura et al.
(Continued)

FOREIGN PATENT DOCUMENTS

EP 0731163 9/1996
EP 1113271 7/2001
(Continued)

OTHER PUBLICATIONS

Kato et al., "Comparison of neuronal cell adhesiveness of materials in the diX (Parylene) family", Neuroscience Letters 464 (2009) p. 26-28.*
(Continued)

*Primary Examiner* — Peter D Mulcahy
*Assistant Examiner* — Henry Hu
(74) *Attorney, Agent, or Firm* — Fish & Richardson P.C.

(57) ABSTRACT

Provided is: a cell culture membrane, which is free from materials derived from living organisms, can easily be industrially mass-produced, exhibits superior long-term storage properties and chemical resistance, has excellent cell adhesion properties and long-term culture properties and is capable of replicating a cell adhesion morphology that is similar to that of collagen derived from living organisms and being used for conventional cell cultivation. Also provided are a cell culture substrate, and a method for manufacturing the cell culture substrate. In the present invention, as a cell adhesion layer, a polymer membrane represented by formula (I) is formed on the base of a cell culture substrate so as to have a membrane thickness equal to or greater than 0.2 μm (in the formula, R1 and R2 represent a —$(CH_2)_n$—$NH_2$ moiety (n is an integer of 1-10 inclusive.) or H, with at least one of R1 and R2 being a —$(CH_2)_n$—$NH_2$ moiety. Moreover, l and m are positive integers expressing polymerization degree).

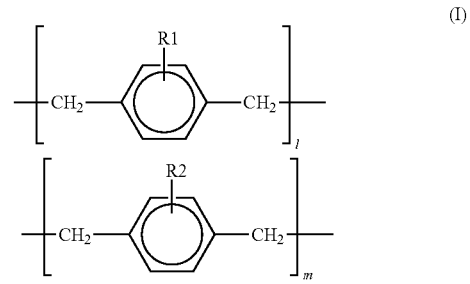

11 Claims, 14 Drawing Sheets

(51) Int. Cl.
*C12N 5/00* (2006.01)
*C12M 1/00* (2006.01)

(56) References Cited

U.S. PATENT DOCUMENTS

| | | | |
|---|---|---|---|
| 2009/0042295 A1* | 2/2009 | Ohya et al. | 435/402 |
| 2009/0242125 A1* | 10/2009 | Paik et al. | 156/345.12 |
| 2011/0097793 A1 | 4/2011 | Suzuki et al. | |
| 2011/0236745 A1* | 9/2011 | Brant et al. | 429/145 |

FOREIGN PATENT DOCUMENTS

| | | |
|---|---|---|
| EP | 1260542 | 11/2002 |
| EP | 1260542 A1 * | 11/2002 |
| JP | 06-292568 | 10/1994 |
| JP | 08-243156 | 9/1996 |
| JP | 09-47503 | 2/1997 |
| JP | 2000-507202 | 6/2000 |
| JP | 2001-233977 | 8/2001 |
| JP | 2002-340916 | 11/2002 |
| JP | 2003-212974 | 7/2003 |
| JP | 2007-322219 | 12/2007 |
| JP | 2008-035806 | 2/2008 |
| WO | 97/20569 | 6/1997 |
| WO | 2009/144928 | 12/2009 |

OTHER PUBLICATIONS

Coelho et al., "Fibroblasts remodeling of type IV collagen at a biomaterials interface", Biomaterials Science, The Royal Society of Chemistry 2013 (9 pages).
Hoshino et al., "Neurite Outgrowth of PC12Cells on diX (Parylene) Family Materials", Biotechnol. Prog., 2012, vol. 28, No. 2, p. 587-590.
International Search Report for PCT/JP2012/066075 dated Jul. 17, 2012.
IPRP for PCT/JP2012/066075 dated Dec. 24, 2013 with English translation.
Saisei-igaku no Ouyo no, Genjo to Kadai, Pharma Media vol. 18, No. I, 2000, p. 25-29, , with partial English translation.
Shirakata et al., The Journal of Clinical Science vol. 34, No. 9, 1998, p. 1283-1290 with partial English translation.
Tissue Engineering, The Univ. of Nagoya Press, Oct. 10, 1999, p. 107-117, p. 118-127 with partial English translation.
Written Opinion for PCT/JP2012/066075 dated Jul. 17, 2012 with English translation.

* cited by examiner

CELL CULTURE MEMBRANE, CELL CULTURE SUBSTRATE, AND METHOD FOR MANUFACTURING CELL CULTURE SUBSTRATE

FIELD OF THE INVENTION

This invention relates to a cell culture membrane, a cell culture substrate and a method for manufacturing such a cell culture substrate, and more particularly concerns a substrate that is desirably used for growing and cultivating cells for use in various fields, such as biology, medicine, pharmacy, immunology, etc., and a cell culture membrane that is desirably used for cultivating functional organ cells, which, in addition to general established cell strains, is desirably applied to embryonic stem cells (ES cells) of rodents such as mice and rats and primates such as monkeys and human beings, artificial skins, artificial bones and artificial organs, and a cell culture substrate, as well as a method for manufacturing such a cell culture substrate.

The present application asserts priority rights based on JP Patent Application 2011-140961 filed in Japan on Jun. 24, 2011. The total contents of disclosure of the patent application of the senior filing date are to be incorporated by reference into the present application.

BACKGROUND OF THE INVENTION

Conventionally, various kinds of animal and plant cells have been cultivated, and various modes of cultivation techniques have also been examined. The cell culture technique is a basic technique for use in many fields that deal with organisms. In particular, in the field of life science, the technique has become an indispensable technique for developing drugs and for clarifying pathologic mechanisms. In recent years, various examinations have been carried out not only on cell culture techniques for research purposes, but also on industrially productive culture methods for use in various fields, such as biology, medicine, pharmacy, immunology, etc. Moreover, in such a field as a medical field or the like, studies have been carried out in which organism cells are cultivated and the resulting cells are utilized as alternative organs, such as artificial organs, artificial teeth and bones, artificial skins, or the like.

In such cell cultivation, a cultivating process is normally carried out together with a culture solution serving as nutritive components in a predetermined container. The cell cultivation is mainly classified into two types depending on its natures, that is, one type in which the cultivation is carried out in a floating state in the culture solution and the other type in which the cultivation is carried out in an adhered state onto the bottom surface of the container. Most of animal cells have such adhesion dependence as to adhere to a substance and to be grown thereon, and in general, cannot survive for a long time in a floating state in vitro. For this reason, in order to cultivate cells having such adhesion dependence, a substrate that allows cells to adhere thereto is required.

As the cell culture substrates, petri dishes, flasks, multiplates, or the like are generally used in the research laboratories. These instruments are mainly prepared as polystyrene molded products with surfaces that are subjected to a low-temperature plasma treatment, a corona discharge treatment or the like so as to provide hydrophilicity thereto, and these products are commercially available. In the case of anchorage dependent cells, these instruments are widely used for cultivation of fibroblasts, smooth muscle cells, vascular endothelial cells, corneal cells or the like, regardless of established cells and primary cells. Moreover, with respect to vasculature cells, these instruments are also widely used for so-called non-anchorage dependent floating cells that are established lymphatic corpuscles.

However, although growth of cells are observed on these cell culture instruments, the growth thereof is sometimes insufficient or the growth morphology of cells is disadvantageous in some cases depending on the kinds of cells. In particular, this defect is in particular conspicuous in the primary cultivation. Therefore, in many cases, the culture surface is coated with an extracellular matrix, such as collagen, gelatin or the like, or an adhesive agent such as fibronectin, laminine, vitronectin or the like, so as to improve the adhesion properties and growing properties of the cells, thereby solving the above-mentioned problems.

For example, as described in Non-Patent Documents 1, 2, 3, and 4 as well as in Patent Documents 1, 2 and 3, it has been known that, as the cell culture substrate, by using collagen, collagen gel, collagen sponge, a collagen sheet having cross-linked molecules to be formed into a three-dimensional structure, collagen sponge with through-holes formed therein, or the like, coated on a petri dish, human fibroblast cells or human cornification cells are disseminated and cultured thereon, so that a cultured epithelium/epidermis is produced, or a human cornification cell layer is formed on the upper surface of a human fibroblast cell so that a cultured mucous membrane/skin can be produced.

The collagen for use in preparing a collagen coat membrane is a type I collagen derived from animal connective tissues that are made soluble by applying an acid or enzyme thereto. This collagen is coated on a culture dish or the like, and then dried so that a collagen coat membrane is obtained. With respect to the collagen producing this cell culture substrate, for example, the collagen in connective tissues of bovine or swine is made soluble, and extracted collagen is used. However, in recent years, due to problems of BSE (Bovine Spongiform Encephalopathy), Aphtae epizooticae, or the like, the application of these to medical purposes has become difficult. Moreover, these materials derived from living organisms are easily denatured by chemicals such as alcohol, and putrefaction easily progresses therein, making it difficult to store for a long period of time. Furthermore, there have been strong demands for a cell culture method whose cell growth efficiency is further improved in comparison with a cell culture method in which these conventional cell culture substrates are used.

Moreover, in a cultivation of nervous-system cells, in many cases, the culture surface is coated with polylysine such as poly-D-lysine, poly-L-lysine, or the like, and the cultivating process is carried out. When coated with the polylysine, nervous-system cells are efficiently adhered, and in the case of established nervous-system cells, good growing morphology is preferably provided, with neurites being expanded in a high degree. Moreover, in a primary cultivation of brain cells of a rat fetus, neurites are desirably expanded, with a high degree of cell stabilization, so that a long-term cultivation can be carried out.

In this manner, although polylysine has desirable properties for cultivation of nervous-system cells, its defect is instability. That is, in the case when coated onto a general-use culture instrument as described above, the effect of polylysine is devitalized in two weeks when stored at room temperature, and in one month even when stored at 4° C. Moreover, this instability makes it difficult to carry out a sterilizing process after the coating process. For this reason, in order to use a culture instrument coated with polylysine, by using a time-consuming method in which a sterilizing operation has to be carried out on a culture instrument that has been preliminarily sterilized, polylysine needs to be coated thereon before use, and the resulting defect is that even when stored in a refrigerator, the usable period is limited only to about one month.

In this manner, in an attempt to coat the culture instrument with polylysine, problems arise in the stability and operability of polylysine, and in an attempt to sell the cell culture instrument preliminarily coated with polylysine on the market, high costs are required because of a number of jobs that have to be carried out under sterilized environments and difficulty in storing and managing the products after having been coated.

In view of these circumstances, as described in Patent Document 4, in order to solve the above-mentioned defects, the present inventors have proposed a cell culture substrate that has a structure containing a polymer having an amino group obtained by allowing a polymer containing an amino group capable of forming at least one Schiff base to react with a monomer unit of polyformyl paraxylylene.

However, the cell culture substrate produced by the aforementioned technique has a defect in that the reproducibility of cell adhesion is hardly obtained depending on conditions in which the Schiff base is made to react with polyformyl paraxylylene. Moreover, since the process of allowing the Schiff base to react after the coating process of polyparaxylylene is included, the number of processes increases, resulting in high costs.

Additionally, with respect to applied examples of polyparaxylylene, Patent Documents 5 and 6 disclose that to a product having a surface coated with polyparaxylylene, gigantic molecules such as protein are adsorbed so as to utilize the resulting product as a reaction container and that by utilizing its biological compatibility, this product is used as one portion of an intravital device for transporting insulin to a diabetic. Moreover, as described in Patent Documents 7 and 8, it has been known that a derivative membrane of polyparaxylylene having a surface with an amino group or an aminomethyl group formed thereon is utilized as a DNA chip-use binder.

In this case, as the roles of the substrate for use in cell cultivation, properties for allowing cells to adhere and for cultivating the cells are required. For this reason, Patent Document 6 has disclosed a technique in which the cell adhesion surface of an actual growing medium is coated with collagen so as to obtain an adhesion property. Moreover, general polyparaxylylene derivatives, such as polyparaxylylene, polymonochloroparaxylylene and polydichloroparaxylylene, as described in Patent Documents 5 and 6, have hardly any adhesion properties to cells, and are not suitable for the cell culture application.

In this manner, no cases have been reported in which a polyparaxylylene membrane, as it is, is utilized as a cell culture substrate, without being subjected to any chemical treatment, and in Patent Documents 7 and 8 as well, neither descriptions nor implications indicating that these derivatives are suitable for the cell culture application are found. In addition to these, as described earlier, the substrate needs to have high adhesion property to cells and it is essential for the substrate to adhere cells in a desirable adhesion morphology to be grown, and its required performances are completely different from those of techniques described in Patent Documents 7 and 8, in which cells are desirably joined to DNA probes so as to prevent them from being peeled off.

PRIOR-ART DOCUMENTS

Patent Documents

PTL 1: Japanese Patent Application Laid-Open No. 6-292568
PTL 2: Japanese Patent Application Laid-Open No. 8-243156
PTL 3: Japanese Patent Application Laid-Open No. 9-47503
PTL 4: Japanese Patent Application Laid-Open No. 2008-35806
PTL 5: Japanese Patent Application Laid-Open No. 2001-233977
PTL 6: Japanese Patent Application Laid-Open No. 2000-507202
PTL 7: Japanese Patent Application Laid-Open No. 2002-340916
PTL 8: Japanese Patent Application Laid-Open No. 2003-212974

Non-Patent Documents

Non-Patent Document 1: Clinical Science, No. 9 Vol. 34, written by Youji Shirakata/Kouji Hashimoto: Reproductive Medicine, X. ambustion and hydroa treatments using reproduction mechanisms of skin and epidermis and a cultivated epidermis sheet, P1283 to P1290.

Non-Patent Document 2: "Basis and Application of Tissue Engineering Fiber Engineering", edited by Minoru Ueda, written by Kyouichi Matsuzaki/Norio Kumagai: Culture Skin, P107 to 117, issued on 1999 Oct. 10 by Nagoya University Press Non-Patent Document 3: Hata Kenichiro/Minoru Ueda: Skin/Mucous Membrane Pharma Media Vol. 18, No. 1 2000 P25 to P29 2000

Non-Patent Document 4: "Basis and Application of Tissue Engineering Fiber Engineering", edited by Minoru Ueda, written by Kenichiro Hata/Minoru Ueda: Oral Cavity Mucous Membrane, P118 to 127, issued on 1999 Oct. 10 by Nagoya University Press

SUMMARY OF THE INVENTION

Therefore, an object of the present invention is to provide a cell culture membrane that is free from materials derived from living organisms, can easily be industrially mass-produced, exhibits superior long-term storage properties and chemical resistance, has excellent cell adhesion properties and long-term culture properties and is capable of replicating a cell culture morphology that is similar to that of collagen derived from living organisms and being generally known as cell culture membrane, and a cell culture substrate, as well as a method for manufacturing such a cell culture substrate.

In order to solve the above-mentioned problems, the inventors of the present invention have conducted various researches, and found that by coating a base with a polyparaxylylene membrane having an aminoalkyl group to a predetermined thickness or more, it is possible to exert peculiar cell adhesion properties, thereby completing the present invention.

That is, a cell culture membrane in accordance with the present invention is provided with a polymer membrane that is composed of a structural unit represented by the following formula (I) and formed on a base, with a membrane thickness of 0.2 μm or more.

[Formula 1]

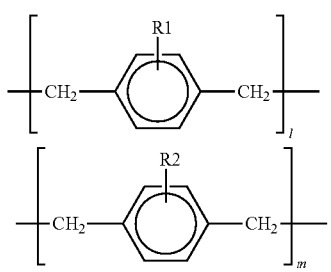

(I)

(in the formula, R1 and R2 represent a —(CH$_2$)$_n$—NH$_2$ moiety (n is an integer of 1-10 inclusive.) or H, with at least one of R1 and R2 being a —(CH$_2$)$_n$—NH$_2$ moiety. Moreover, l and m are positive integers expressing polymerization degree.)

Moreover, a cell culture substrate in accordance with the present invention is provided with a polymer membrane that is composed of a structural unit represented by the following formula (I) and formed on a base, with a membrane thickness of 0.2 μm or more.

[Formula 2]

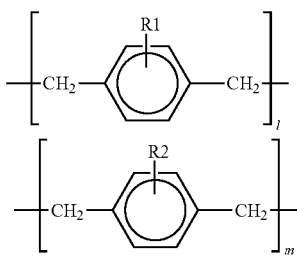

(I)

(in the formula, R1 and R2 represent a —(CH$_2$)$_n$—NH$_2$ moiety (n is an integer of 1-10 inclusive) or H, with at least one of R1 and R2 being a —(CH$_2$)$_n$—NH$_2$ moiety. Moreover, l and m are positive integers expressing polymerization degree.)

Moreover, a method for manufacturing the cell culture substrate in accordance with the present invention is provided with the step of forming a polymer membrane represented by the following formula (I) as a cell adhesion layer with a membrane thickness of 0.2 μm or more.

[Formula 3]

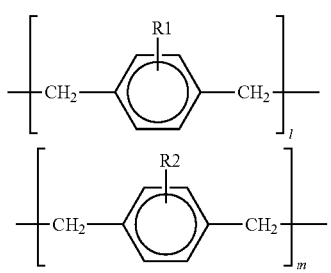

(I)

(in the formula, R1 and R2 represent a —(CH$_2$)$_n$—NH$_2$ moiety (n is an integer of 1-10 inclusive) or H, with at least one of R1 and R2 being a —(CH$_2$)$_n$—NH$_2$ moiety. Moreover, l and m are positive integers expressing polymerization degree.)

In the method for manufacturing the cell culture substrate, the polymer membrane is formed by using a material represented by the following structural formula (II), with being polymerized on a base by using a chemical vapor deposition method.

[Formula 4]

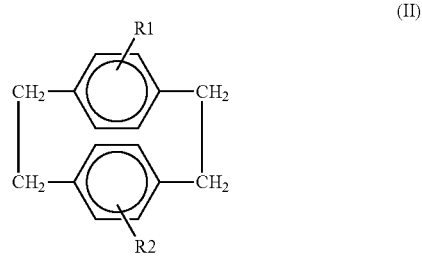

(II)

(in the formula, R1 and R2 represent a —(CH$_2$)$_n$—NH$_2$ moiety (n is an integer of 1-10 inclusive) or H, with at least one of R1 and R2 being a —(CH$_2$)$_n$—NH$_2$ moiety.)

EFFECTS OF INVENTION

In accordance with the present invention, the resulting cell culture substrate has excellent cell adhesion properties and long-term culture properties, without the necessity of using a material derived from living organisms such as collagen, and makes it possible to cultivate cells with a cell adhesion morphology that is similar to that of a material derived from living organisms. Moreover, since no material derived from living organisms is used, it is possible to provide chemical resistance and long-term storage properties and it is also possible to carry out a cultivation process by using a simple method that is easily handled; thus, it becomes possible to store cultivated cells stably for a long period of time without the necessity of a cooling process or the like.

Moreover, since a cell adhesion layer can be formed on a base by using only a process such as a vapor deposition method, it is not necessary to carry out a process under an aseptic environment and a post-process after the coating, and the cell culture substrate can easily be industrially mass-produced and can be provided at low costs. Furthermore, since the cell adhesion layer can be formed on a base having various shapes, such as, for example, a three-dimensional shape, and a base having various material properties, it has a wide application range.

DETAILED DESCRIPTION OF THE INVENTION

The following description will discuss specific embodiments of the present invention. Additionally, modifications may be made in the present invention within a scope not departing from the gist of the present invention.

A cell culture substrate in accordance with the present embodiment has a structure in which a cell adhesion layer is formed on a base, and the cell adhesion layer is provided with a polymer membrane (cell culture base membrane) composed of a structural unit represented by the following formula (I). Moreover, the cell culture substrate is composed of the polymer membrane represented by the following formula (I) formed (membrane-formed) on the base with a membrane thickness of 0.2 μm or more.

[Formula 5]

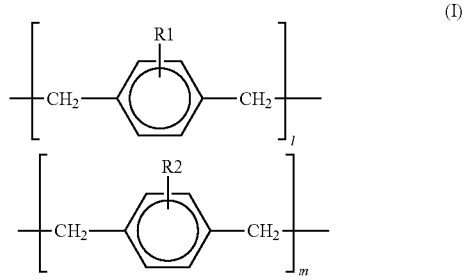

(I)

In the formula (I), R1 and R2 represent a —$(CH_2)_n$—$NH_2$ moiety (n is an integer of 1-10 inclusive.) or H (hydrogen), with at least one of R1 and R2 being a $(CH_2)_n$—$NH_2$ moiety. Moreover, l and m are positive integers expressing polymerization degree.

Although not particularly limited, this cell culture substrate is produced by forming the polymer membrane represented by the above-mentioned formula (I) on a base, for example, by the use of a chemical vapor deposition method, or preferably, a CVD method, or the like.

For example, the cell culture substrate is produced by processes in which a material compound is prepared, the material compound is evaporated and decomposed under a predetermined reduced pressure environment, and this is polymerized and deposited on the base so as to be membrane-formed as a polymer membrane.

As the material compound, for example, a compound represented by the following formula (II) may be used.

[Formula 6]

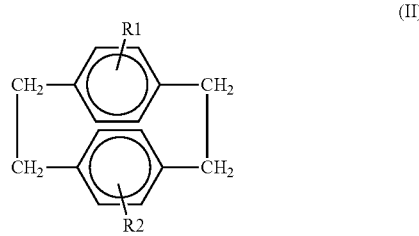

(II)

In the formula (II), R1 and R2 represent a —$(CH_2)_n$—$NH_2$ moiety (n is an integer of 1-10 inclusive.) or H, with at least one of R1 and R2 being a —$(CH_2)_n$—$NH_2$ moiety.

As the compound represented by the formula (II), from the viewpoints of synthesis efficiency, economic rationalization, etc., those compounds of n=1 to 10, preferably, n=1 to 3, may be used. In particular, from the viewpoint of easiness of synthesis, monoaminomethyl(2,2)paracyclophane with R1 of n=1 and R2 of H is preferably used.

Additionally, the compound represented by the above-mentioned formula (II) to be used as a material compound can be synthesized by a conventional method or a method according to a conventional method. For example, the compound may be synthesized by using the method described in Japanese Patent Application Laid-Open No. 2003-212974 or the like. Moreover, a commercially available product as a trade name diX AM (made by Daisan Kasei Co., Ltd.), as it is, may be used.

More specifically, with respect to the method for manufacturing a cell culture substrate in accordance with the present embodiment, the following description will discuss a manufacturing method by the use of a chemical vapor deposition process.

Figure 1:
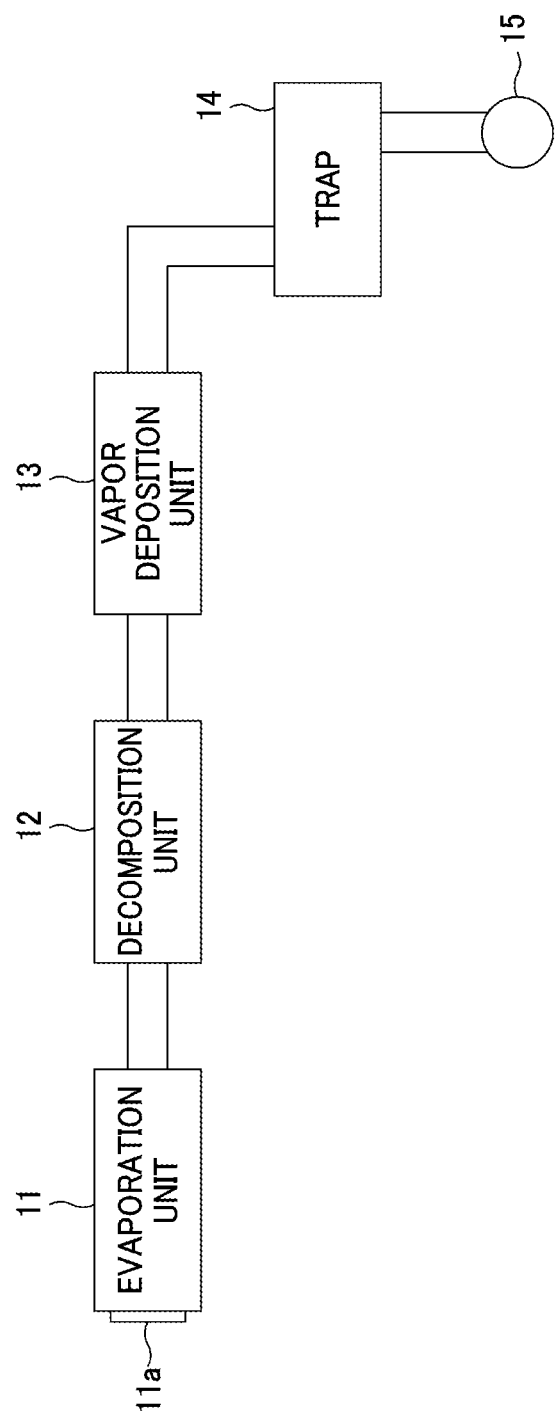
FIG. 1 is a block diagram showing one example of a schematic structure of a device for use in manufacturing a cell culture substrate.

For example, the chemical vapor deposition process may be carried out by using a vapor deposition device 1 as shown in FIG. 1. The vapor deposition device 1 is provided with an evaporation unit 11, a decomposition unit 12 and a vapor deposition unit 13. The evaporation unit 11 is provided with a vapor deposition material loading inlet 11a for use in introducing an evaporation material (material compound), and to the vapor deposition unit 13, a vacuum pump 15 is further connected through a trap 14.

In the chemical vapor deposition using the vapor deposition device 1, first, a solid-state evaporation material, for example, represented by the above-mentioned formula (II), is introduced into the evaporation unit 11. In the evaporation unit 11, by heating the evaporation unit 11 so as to raise the inner temperature to a temperature at which the evaporation material is evaporated, for example, to 80 to 200° C., preferably, to 100 to 180° C., so that the compound of the evaporation material is evaporated to generate a material gas.

Next, the generated material gas is introduced into the decomposition unit 12. In the decomposition unit 12, by heating the introduced material gas to its decomposing temperature, for example, to 500 to 800° C., more preferably, to 600 to 750° C., so that the material gas is thermally decomposed into a monomer gas.

Next, the resulting monomer gas is introduced into the vapor deposition unit 13. Moreover, a base, such as a cell culture plate or the like, is introduced into the vapor deposition unit 13. The inside of the vapor deposition unit 13 is maintained at a predetermined vacuum degree, for example, 1 to 20 Pa, preferably, 2 to 10 Pa. Moreover, in the vapor deposition unit 13, the introduced material monomer gas is made in contact with the base to be polymerized on the base surface so that a polymer membrane represented by the above-mentioned formula (I) is formed with a membrane thickness of a predetermined thickness or more.

Thus, a cell culture substrate on which the polymer membrane represented by the above-mentioned formula (I) is formed on the base as the cell adhesion layer can be produced.

Additionally, prior to the formation of the polymer membrane represented by the above-mentioned formula (I) on the base of the cell culture substrate as a cell adhesion layer, for example, a chemical vapor deposition material, such as chloro-substituted (2,2)paracyclophane, preferably, dichloro (2,2)paracyclophane, may be formed thereon as a base material. With this arrangement, the strength of the cell adhesion layer can be improved, and the adhesion to the base can also be improved.

In this manner, in accordance with the method for manufacturing the cell culture substrate by forming the polymer membrane represented by the above-mentioned formula (I) on the base by using the chemical vapor deposition method, since the formation of the polymer membrane is carried out by allowing the monomer gas obtained by evaporating and thermally decomposing the material to be made in contact with the base surface forming a cell culture substrate, it is possible to form a polymer membrane on the base uniformly with a predetermined membrane thickness, and it also becomes possible to apply this to a base having a complicated structure, such as a three-dimensional solid structure.

Additionally, as the base, although not particularly limited, glass or silicon, or polymers, such as polycarbonates (polyethylene terephthalate, cellulose acetate, bisphenol A, etc.), polystyrene, polymethyl methacrylate, silicone rubber (polydimethyl siloxane, etc.), or the like, are preferably used. Moreover, other materials, such as paper and metal, or fibers or the like, may be used as the base. Furthermore, as the base to be inserted into the body, or for use in configuring a three-dimensional structure, those having properties, such as tissue compatibility and biodegradability, are preferably used. Additionally, the base thus prepared may be subjected to a silane coupling treatment by the use of a conventional technique, or may be subjected to a conventional surface treatment, such as an oxygen plasma treatment. Thus, the adhesion to the cell adhesion layer can be improved.

In this case, as described earlier, the polymer membrane to be formed on the base of the cell culture substrate is preferably designed to have a membrane thickness of about 0.2 μm or more, more preferably, about 0.3 μm or more. In this manner, by forming the polymer membrane represented by the aforementioned formula (I) on the base with a membrane thickness of about 0.2 μm or more, the adhesion morphology of the cultivated cell can be developed similarly to that of mesenchymal cells. That is, it is possible to form a culture environment suitable for a mesenchymal-type cell.

The cell adhered similarly to that of a mesenchymal cell exerts high adhesion to a polymer membrane that is an extracellular matrix. Therefore, in accordance with the cell culture substrate capable of providing a cell adhesion morphology that is similar to that of mesenchymal cells, it becomes possible to further improve the adhesion strength of cells and consequently to grow cells in a stable manner. Moreover, by providing the cell adhesion morphology that is similar to that of mesenchymal cells, the migrating capability of the adhered cells can be improved so that a large amount of cells can be grown and cultivated even within a limited space. Furthermore, upon cultivating functional tissue cells for use in embryonic stem cells (ES cells), artificial skins, artificial bones, artificial organs, etc., since by providing a cell adhesion morphology that is similar to that of mesenchymal cells, progress of differentiation can be controlled, the cell culture substrate can be applied to the cultivation of these cells desirably.

Additionally, the upper limit of the membrane thickness of the polymer membrane formed on the base is not particularly limited as long as the above-mentioned effects can be obtained. However, from the viewpoint of economic rationalization or the like, the thickness is desirably set to 10 μm or less.

As described above, the cell culture substrate in accordance with the present embodiment is provided with the polymer membrane composed of the structural unit represented by the above-mentioned formula (I) formed on a base as a cell adhesion layer, with a membrane thickness of 0.2 μm or more. In accordance with this cell culture substrate, it is possible to adhere cells thereto stably with superior adhesion strength, and consequently to cultivate cells with superior reproducibility for a long period of time, while preventing cells from being peeled off. Moreover, since the cells can be adhered in an adhesion morphology that is similar to that of mesenchymal cells, the cells can be grown effectively.

Moreover, different from a conventional structure, since no materials such as collagen derived from living organisms are used, chemical resistance is achieved, with long-term storage properties being also achieved. That is, materials derived from living organisms, such as collagen, which have been conventionally used as a cell culture substrate, have a defect of being easily denatured and devitalized by chemicals, such as alcohol or the like. Moreover, since putrefaction soon progresses therein because these materials are derived from living organisms, it is required for cooling them to a predetermined temperature or less at the time of storage, and it is difficult to store them for a long time even under a cooled environment. In contrast, since the cell culture substrate in accordance with the present embodiment uses no materials derived from living organisms, it is neither denatured nor devitalized even by alcohol or the like, and it is used for cultivation by simply carrying out pretreatments, such as sterilizing and washing treatments, by using chemicals such as alcohol or the like. Moreover, the cultivated cells can be stored stably for a long period of time without the necessity of cooling or the like.

Furthermore, since the cell culture substrate in accordance with the present embodiment can be produced by forming the aforementioned polymer membrane on a base by simply carrying out a process such as a chemical vapor deposition process or the like, it is not necessary to carry out a chemical treatment in a separate manner after a treatment carried out in a sterilized environment and a coating process of the resulting cell adhesion layer, so that it is easily industrially mass-produced by using simple processes.

Additionally, prior to the cultivation, it is possible to carry out not only the above-mentioned simple pretreatments, such as sterilizing and washing treatments by using chemicals such as alcohol or the like, but also certainly a sterilizing treatment on the produced cell culture substrate. With respect to the sterilizing method, not particularly limited, it is carried out by using an autoclave, gamma rays, electron beams, EOG (ethylene oxide gas) or the like, and the sterilizing process by using an electron beam is preferably used, or an electron sterilizing treatment under non-oxygen is more preferably used.

EXAMPLES

The following description will discuss examples of the present invention; however, the present invention is not intended to be limited by the examples described hereinbelow.

<Formation of Substrate Having Cell Adhesion Layer•Cultivation of HepG2 Cell Derived from Human Hepatic Cancer>

Example 1

(Formation of Substrate Having Cell Adhesion Layer)
(1) Preparation of Base

As a base, a commercially available 24 WELL cell culture multi-well plate (TC (Tissue Culture) processed product, made by Becton Dickinson and Company.) made of polystyrene was prepared, and as a raw material for a cell adhesion layer, monoaminomethyl(2,2)paracyclophane (dix AM, made by Daisan Kasei Co., Ltd.), which was a compound represented by the following chemical formula (II), with R1 being indicated by a —CH$_2$NH$_2$ moiety and R2 being indicated by H, was prepared.

[Formula 7]

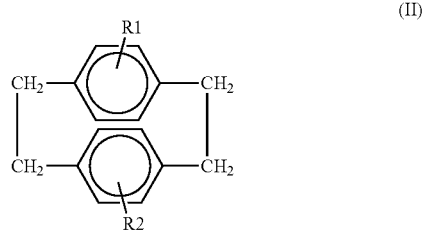

(II)

(2) Formation of Polymer Membrane

Next, in a vapor deposition device 1 as shown in FIG. 1, 8 g of monoaminomethyl(2,2)paracyclophane serving as a solid-state vapor deposition material thus prepared was introduced into an evaporation unit 11 from a vapor deposition material loading inlet 11a. Moreover, the 24 WELL cell culture multi-well plate made of polystyrene serving as a base was introduced into a vapor deposition unit 13. Thereafter, with the inside of the device system being maintained at a vacuum degree of 1.7 Pa by using a vacuum pump 15, the device was gradually heated to a temperature in a range of 110° C. to 115° C. Thus, the vapor deposition material was evaporated to form a dimer gas so that a material gas was generated.

Next, the generated material gas was introduced into a decomposition unit 12 heated to 600° C. In this decomposition unit 12, the introduced material gas was formed into a monomer gas (III) through thermal decomposition, as shown in the following reaction scheme.

Next, the resulting monomer gas (III) was introduced into the vapor deposition unit 13. The inside of the vapor deposition unit 13 was maintained at the maximum degree of vacuum of 6 Pa. Then, the introduced monomer gas (III) was polymerized on the surface of the 24 WELL cell culture multi-well plate made of polystyrene, which was placed inside the vapor deposition unit 13 so that a membrane of a polymer represented by the above-mentioned formula (I) was formed thereon, as shown in the following reaction scheme; thus, a cell culture substrate was produced. At this time, the average membrane thickness of the polymer membrane thus formed was 1.1 μm.

(Cultivation of HepG2 Cell Derived from Human Hepatic Cancer)

With respect to the cell culture substrate obtained as described above, 2 ml of 70% ethanol was put in each of the wells of the 24 WELL plate, and each of these was stationarily placed inside a clean bench for 15 minutes. Thereafter, the well was washed with sterilizing water, and dried so that after the alcohol sterilizing process, HepG2 cells derived from human hepatic cancer were cultivated. As cultivating conditions, cells of 8.0×10$^4$ were disseminated in each WELL of the 24 WELL plate, a DMEM (low glucose) to which a suspension of 10% FBS and 1% penicillin-streptomycin-amphotericin B, and 1% of non-essential amino acids were added was used as a culture medium, and the cultivation was carried out under an atmosphere of 5% CO$_2$.

Figure 2:
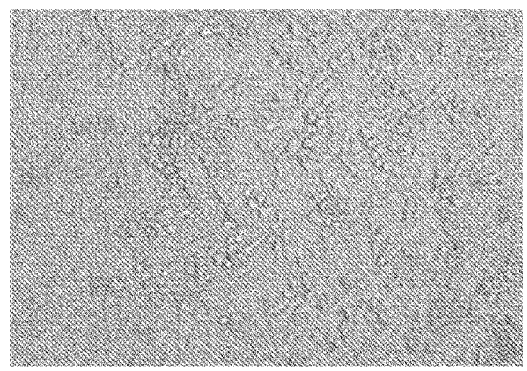
FIG. 2 is a microscopic photograph showing a cultivated state 3 days after the cultivation of example 1.
Figure 3:
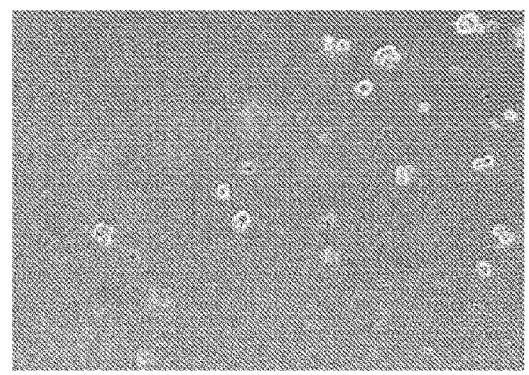
FIG. 3 is a microscopic photograph at ×100 magnification showing a cultivated state 3 days after the cultivation onto polymonochloroparaxylylene of comparative example 1.
Figure 4:
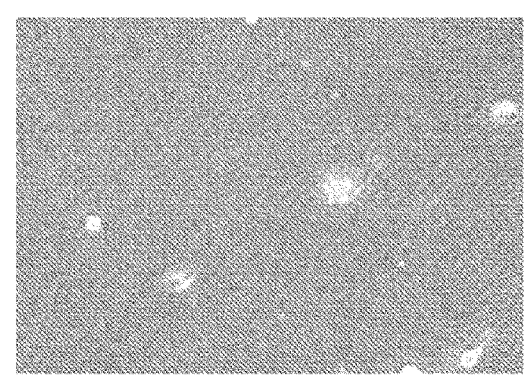
FIG. 4 is a microscopic photograph at ×100 magnification showing a cultivated state 3 days after the cultivation onto polyparaxylylene of comparative example 1.
Figure 5:
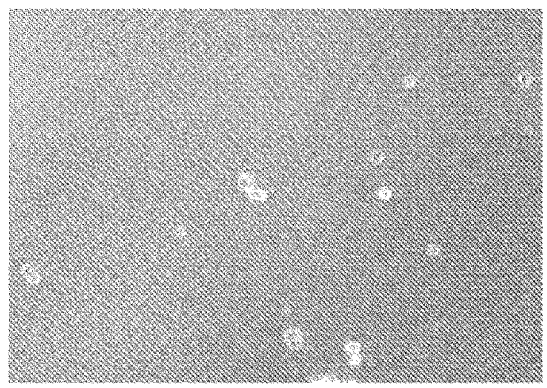
FIG. 5 is a microscopic photograph at ×100 magnification showing a cultivated state 3 days after the cultivation onto polytetrafluoroparaxylylene of comparative example 1.
Figure 6:
FIG. 6 is a microscopic photograph at ×100 magnification showing a cultivated state 3 days after the cultivation onto a copolymer of monoaminoparaxylylene and paraxylylene of comparative example 1.
Figure 7:
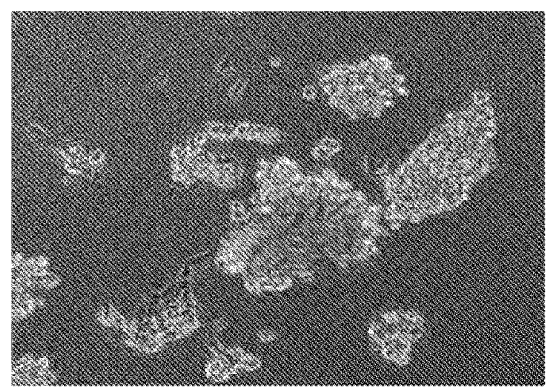
FIG. 7 is a microscopic photograph at ×100 magnification showing a cultivated state 3 days after the cultivation onto a copolymer of monoformylparaxylylene and paraxylylene of comparative example 1.

FIG. 2 shows a cultivated state 3 days after the cultivation carried out in example 1.

Comparative Example 1

<Formation of Cell Culture Substrate by Another Polyparaxylylene Derivative•Cultivation of HepG2 Cell>

In comparative example 1, five kinds of vapor deposition materials, i.e., dichloro(2,2)paracyclophane (trade name: diX C, made by Daisan Kasei Co., Ltd.), (2,2)paracyclophane (trade name: diX N, made by Daisan Kasei Co., Ltd.), octafluoro(2,2)paracyclophane (trade name: diX SF, made by Daisan Kasei Co., Ltd.), monoamino(2,2)paracyclophane (trade name: diX A, made by Daisan Kasei Co., Ltd.), monoformyl(2,2)paracyclophane (trade name: diX H, made by Daisan Kasei Co., Ltd.), were prepared, and a polymer membrane was formed thereon by using the same method as that of example 1 so that cell culture substrates were produced.

Next, by using the resulting five kinds of test samples (cell culture substrates), culture tests of HepG2 cells derived from human hepatic cancer were carried out under the same culture conditions as those of example 1.

FIGS. 3 to 7 respectively show cultivated states 3 days after the cultivation carried out by using copolymers between each of polymonochloroparaxylylene, polyparaxylylene, polytetrafluoroparaxylylene and monoaminoparaxylylene, and paraxylylene of comparative example 1, as well as a copolymer between monoformylparaxylylene and paraxylylene.

[Formula 8]

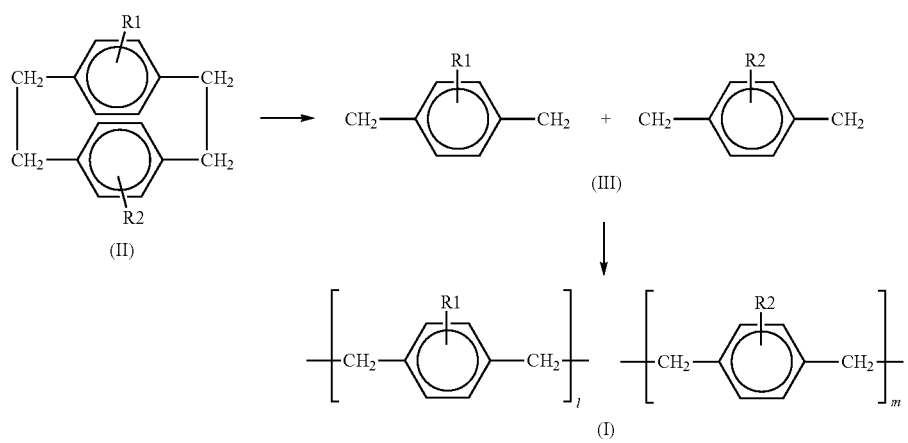

Comparative Example 2

(Cultivation of HepG2 Cell by Using Generally-Used Cell Culture Substrate)

In comparative example 2, by using the 24 WELL cell culture multi-well plate (TC (Tissue Culture) processed product) generally used for cell cultivation, a culture test for HepG2 cells derived from human hepatic cancer was carried out under the same conditions as those of example 1.

Figure 8:
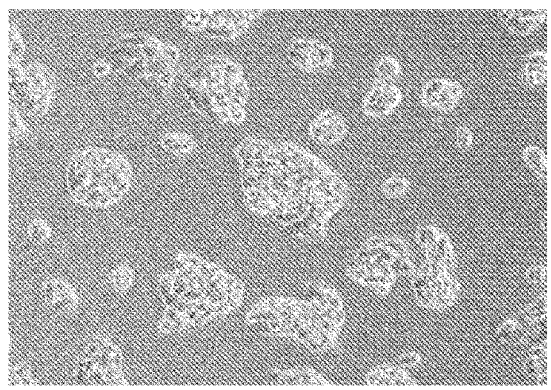
FIG. 8 is a microscopic photograph at ×100 magnification showing a cultivated state 3 days after the cultivation of comparative example 2.

FIG. 8 shows a cultivated state 3 days after the cultivation carried out in comparative example 2.

Reference Example 1

(Cultivation of HepG2 Cell by Using Cell Culture Substrate Coated with Collagen)

In reference example 1, by using a 24 WELL cell culture multi-well plate made of polystyrene and coated with collagen, which was generally used for cell cultivation, a culture test for HepG2 cells derived from human hepatic cancer was carried out under the same conditions as those of example 1.

Figure 9:
FIG. 9 is a microscopic photograph at ×100 magnification showing a cultivated state 3 days after the cultivation of reference example 1.

FIG. 9 shows a cultivated state 3 days after the cultivation carried out in reference example 1.

Table 1 shows results of cultivations of HepG2 cells derived from human hepatic cancer, carried out in example 1, comparative examples 1 and 2, and reference example 1. Additionally, in the evaluations of cell adhesion capability of Table 1, "⊚", "○", "Δ" and "X" respectively indicate adhesion strengths, and the adhesion strengths satisfy ⊚>○>Δ>X. In this case, "X" indicates that no cell adhesion capability is exerted.

adhesion properties are exerted, or even when adhered, its adhesion strength is very weak, and that the resulting membranes are not suitable for the cell culture substrate. In contrast, the copolymer of monoaminomethylparaxylylene and paraxylylene of example 1 has superior cell adhesion properties, and its adhesion strength is very strong. Moreover, the copolymer of monoaminomethylparaxylylene and paraxylylene of example 1 has superior cell adhesion properties and also provides a cell adhesion morphology that is similar to that of mesenchymal cells, in the same manner as in collagen coat shown in reference example 1.

<Cultivation of HepG2 Cells with Membrane-Thickness of Cell Adhesion Layer being Changed>

Example 2

By using the same method as that of example 1, polymer membranes respectively having membrane thicknesses of 0.1 μm, 0.2 μm and 0.3 μm were formed from monoaminomethyl(2,2)paracyclophane, and cell culture substrates were respectively produced; thus, cultivations of HepG2 cells derived from human hepatic cancer were carried out under the same conditions as those of example 1.

Figure 10:
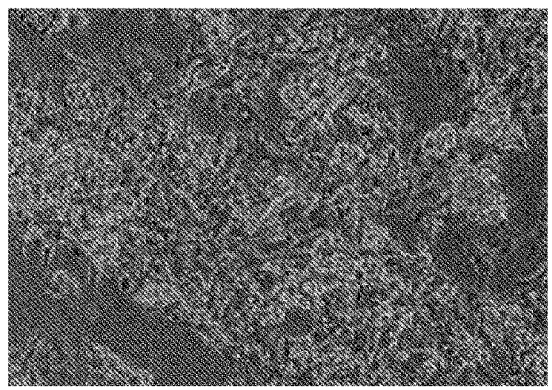
FIG. 10 is a microscopic photograph at ×100 magnification showing a cultivated state 3 days after the cultivation of a sample having a membrane thickness of 0.1 µm of example 2.
Figure 11:
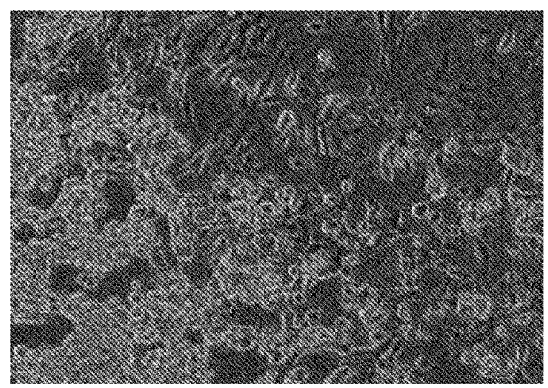
FIG. 11 is a microscopic photograph at ×100 magnification showing a cultivated state 3 days after the cultivation of a sample having a membrane thickness of 0.2 µm of example 2.
Figure 12:
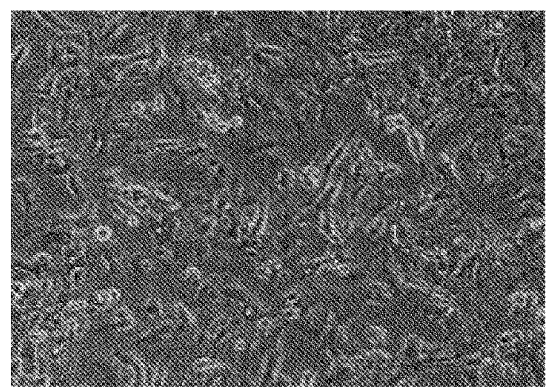
FIG. 12 is a microscopic photograph at ×100 magnification showing a cultivated state 3 days after the cultivation of a sample having a membrane thickness of 0.3 µm of example 2.

FIGS. 10 to 12 show cultivated states 3 days after the cultivations carried out in example 2, with the membrane thicknesses being set to 0.1 μm, 0.2 μm and 0.3 μm.

Table 2 shows results of cultivations carried out by using cell culture substrates on which the polymer membranes having the respective membrane-thicknesses were formed. Additionally, this Table 2 also shows the results of cultivations in the aforementioned example 1 and comparative example 2 in combination. In the evaluations of cell adhe-

TABLE 1

|  | Example 1 | Comparative Example 1 | | | | | Comparative Example 2 | Reference Example 1 |
| --- | --- | --- | --- | --- | --- | --- | --- | --- |
| Cell adhesion layer | Copolymer of mono-aminomethyl-paraxylylene and paraxylylene | Poly-monochloro-paraxylylene | Poly-paraxylylene | Polytetrafluoro-paraxylylene | Copolymer of monoamino-paraxylylene and paraxylylene | Copolymer of monoformyl-paraxylylene and paraxylylene | TC processed product | Collagen coat |
| Membrane thickness | 1.1 μm | 2.4 μm | 0.9 μm | 0.5 μm | 1.2 μm | 0.3 μm | — | — |
| Cell adhesion capability | ⊚ | X | X | X | X | Δ | ○ | ⊚ |
| Adhesion morphology | Mesenchymal cell state | Unanalyzable | | | | Epithelium cell state | Epithelium cell state | Mesenchymal cell state |

As clearly indicated by the cultivation results shown in Table 1, it is found that among polyparaxylylene derivative membranes, except for the copolymer of monoaminomethylparaxylylene and paraxylylene of example 1, no cell sion capability of Table 2, "⊚" and "○" respectively indicate that cell adhesion capabilities are exerted in the same manner as in the aforementioned Table 1, and the adhesion strengths satisfy ⊚>○.

TABLE 2

|  | Example 2 | | | Example 1 | Comparative Example 2 |
| --- | --- | --- | --- | --- | --- |
| Cell adhesion layer | Copolymer of monoaminomethylparaxylylene and paraxylylene | | | | TC processed product |
| Membrane thickness | 0.1 μm | 0.2 μm | 0.3 μm | 1.1 μm | — |
| Cell adhesion capability | ○ | ⊚ | ⊚ | ⊚ | ○ |

TABLE 2-continued

|  | Example 2 | | | Example 1 | Comparative Example 2 |
|---|---|---|---|---|---|
| Adhesion morphology | Epithelium cell state | Mixed state of epithelium cell state and mesenchymal cell state | Mesenchymal cell state | Mesenchymal cell state | Epithelium cell state |

As clearly indicated by the cultivation results shown in Table 2, the cell adhesion capability was exerted in any of the membrane thicknesses. However, in the case of the membrane thickness of the cell adhesion layer of 0.1 μm, there was no difference from the cultivation in the TC processed product of comparative example 2, with its adhesion morphology being similar to that of epithelium cells.

In contrast, in the case of the membrane thickness of the cell adhesion layer of 0.2 μm or more, superior cell adhesion properties were exerted, with its adhesion strength being also very strong, and its adhesion morphology was confirmed to be similar to that of mesenchymal cells so that the cultivated cells were adhered in such a cell morphology as to be desirably grown; thus, the effects of the cell adhesion layer were sufficiently exerted.

<Cultivation of HepG2 Cells by Electron-Beam Sterilizing Treatment Under Non-Oxygen Environment>

Example 3

In accordance with the same method as that of example 1, a polymer membrane with a membrane thickness of 0.6 μm was formed from monoaminomethyl(2,2)paracyclophane so that a cell culture substrate was produced, and by applying an electron beam of 12 kGy thereto under a non-oxygen environment, a sterilizing treatment was carried out, and cultivation of HepG2 cells derived from human hepatic cancer was then carried out under the same culture conditions as those of example 1.

Figure 13:
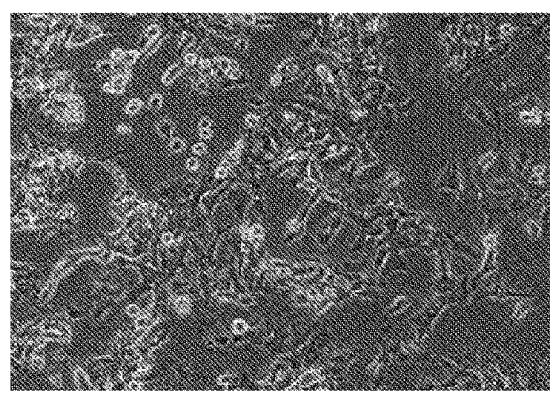
FIG. 13 is a microscopic photograph at ×100 magnification showing a cultivated state 3 days after the cultivation of example 3.

As a result, superior cell adhesion properties were exerted in the same manner as those of example 1, with an adhesion morphology similar to that of mesenchymal cells being provided, so that the effects of the cell adhesion layer were sufficiently exerted. Additionally, FIG. 13 shows a cultivated state 3 days after the cultivation carried out in example 3.

<Cultivation of HepG2 Cells by Lamination of Polyparaxylylene Derivatives>

Example 4

After a polymer membrane of polymonochloroparaxylylene with a membrane thickness of 2.4 μm had been formed on a surface of 24 WELL cell culture multi-well plate made of polystyrene, a polymer membrane with a membrane thickness of 1.1 μm was formed from monoaminomethyl(2,2)paracyclophane by using the same method as that of example 1 so that a cell culture substrate was produced. That is, after polymonochloroparaxylylene had been formed as a base, a polymer membrane was formed by monoaminomethyl(2,2)paracyclophane.

By using the resulting cell culture substrate, cultivation of HepG2 cells derived from human hepatic cancer was carried out under the same culture conditions as those of example 1.

Figure 14:
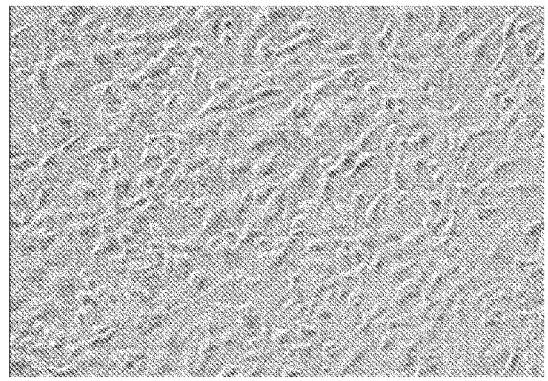
FIG. 14 is a microscopic photograph at ×100 magnification showing a cultivated state 3 days after the cultivation of example 4.

As a result, superior cell adhesion properties were exerted in the same manner as those of example 1, with an adhesion morphology similar to that of mesenchymal cells being provided, so that the effects of the cell adhesion layer were sufficiently exerted. Additionally, FIG. 14 shows a cultivated state 3 days after the cultivation carried out in example 4.

<Long-Term Cultivation of HepG2 Cells>

Example 5

In accordance with the same method as that of example 1, a polymer membrane with a membrane thickness of 1.0 μm was formed from monoaminomethyl(2,2)paracyclophane so that a cell culture substrate was produced, and a long-term culture test of HepG2 cells derived from human hepatic cancer was carried out over 11 days in the longest.

With respect to the culture conditions, a cell culture liquid medium of 1 ml was put in each of the wells of the 24 WELL cell culture multi-well plate with a polymer membrane formed thereon, and HepG2 cells were disseminated thereon and cell-cultivated for 11 days under an atmosphere of 5% $CO_2$ at 37° C. Additionally, as the cell culture liquid medium, a general-use DMEM (low glucose) to which a suspension of 10% FBS and 1% penicillin-streptomycin-amphotericin B and 1% of non-essential amino acids were added was used. Additionally, since the present test was a long-term cultivation, medium exchanges were carried out every other day.

Figure 15:
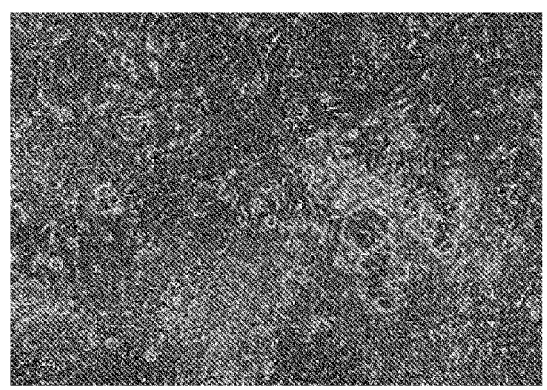
FIG. 15 is a microscopic photograph at ×100 magnification showing a cultivated state 11 days after the cultivation of example 5.

FIG. 15 shows a cultivated state 11 days after the cultivation carried out in example 5.

Comparative Example 3

(Long-Term Cultivation of HepG2 Cells by the Use of Generally-Used Cell Culture Substrate)

In comparative example 3, a 24 WELL cell culture multi-well plate made of polystyrene (TC processed product), which was generally used for cell cultivations, a 24 WELL cell culture multi-well plate made of polystyrene and coated with collagen, and a commercially available plate (PureCoat Amine, made by BD Company.) were used, and long-term culture tests of HepG2 cells derived from human hepatic cancer were carried out thereon under the same culture conditions as those of example 5.

Figure 16:
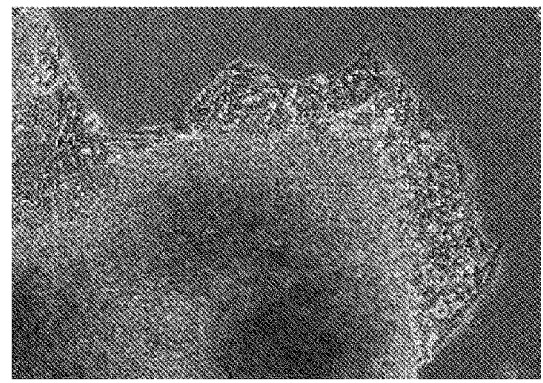
FIG. 16 is a microscopic photograph at ×100 magnification showing a cultivated state 11 days after the cultivation onto a TC processed product of comparative example 3.
Figure 17:
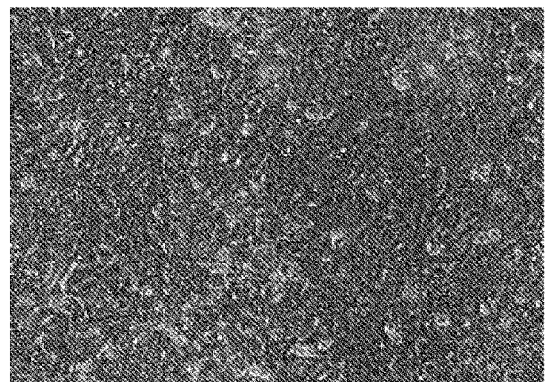
FIG. 17 is a microscopic photograph at ×100 magnification showing a cultivated state 11 days after the cultivation onto a collagen-coated product of comparative example 3.
Figure 18:
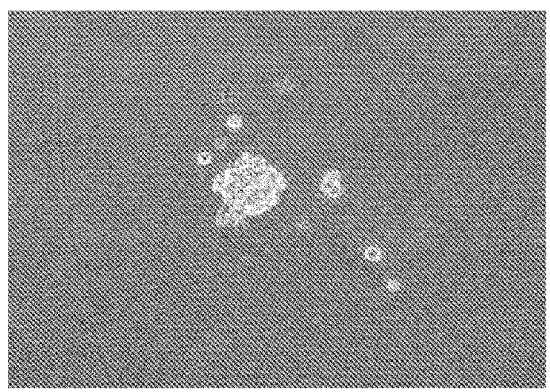
FIG. 18 is a microscopic photograph at ×100 magnification showing a cultivated state 11 days after the cultivation onto a commercially available product of comparative example 3.

FIGS. 16 to 18 show cultivated states 11 days after the cultivations carried out by using the TC processed product, the collagen-coated product and the commercially available product of comparative example 3.

Table 3 shows results of long-term cultivations of HepG2 cells derived from human hepatic cancer that were carried out in example 5 and comparative example 3. In the evaluations of cell adhesion capability of Table 3, both of "⊚" and "○" indicate that cell adhesion capabilities were exerted, and the adhesion strengths satisfy ⊚>○.

TABLE 3

|  | Example 5 | Comparative Example 3 | | |
| --- | --- | --- | --- | --- |
| Cell adhesion layer | Copolymer of monoaminomethylparaxylylene and paraxylylene | TC processed product | Collagen coat | PureCoat Amine made by BD Company |
| Membrane thickness | 1.0 μm | — | — | — |
| Cell adhesion capability | ⊚ | ○ | ⊚ | ⊚ (in the case of short term) |
| Adhesion morphology | Mesenchymal cell state | Epithelium cell state | Mesenchymal cell state | Mesenchymal cell state |
| Long-term culture properties | Presence | Presence | Presence | Absence |

As clearly indicated by the cultivation results shown in Table 3, although the TC processed product of comparative example 3 had a cell adhesion capability, its adhesion strength was weak and there were some cells that were not completely adhered. Moreover, in the TC processed product, the adhesion morphology of cells was exerted in a manner similar to that of epithelium cells, failing to provide a morphology in which cultivated cells were sufficiently grown. In the case of the PureCoat Amine made by BD Company, although the cells were adhered with sufficient strength, with the cells being grown while maintaining the respective morphologies in the respective plates, on a short-term basis, the cells were undesirably peeled off, failing to carry out a long-term cultivation.

In contrast, in example 5, sufficient cell adhesion properties were exerted, with its adhesion strength being also very strong and desirable. Moreover, the adhesion morphology of cells was exerted in a manner similar to that of mesenchymal cells, making it possible to provide a morphology in which cultivated cells are sufficiently grown. Furthermore, the cells were grown for a long period of time, while maintaining the grown cells without being peeled off, so that it was possible to carry out a long-term cultivation.

<Cultivation of Other Cells>

Example 6

(Cultivation of Endothelial Cell HUVEC of Human Umbilical Cord Vein Vascular)

By using the same method as that of example 1, polymer membranes respectively having membrane thicknesses of 0.2 μm and 0.3 μm were formed from monoaminomethyl (2,2)paracyclophane, and cell culture substrates were respectively produced; thus, cultivations of endothelial cell HUVEC of human umbilical cord vein vascular were carried out.

With respect to the culture conditions, a cell culture liquid medium of 1 ml was put in each of the wells of the 24 WELL cell culture multi-well plate on which the polymer membrane was formed, and HUVEC cells were disseminated thereon and the cells were cultivated for 11 days under an atmosphere of 5% $CO_2$ at 37° C. Additionally, as the cell culture liquid medium, an EGM-2 that was generally used at the time of HUVEC cultivation was used.

Figure 19:
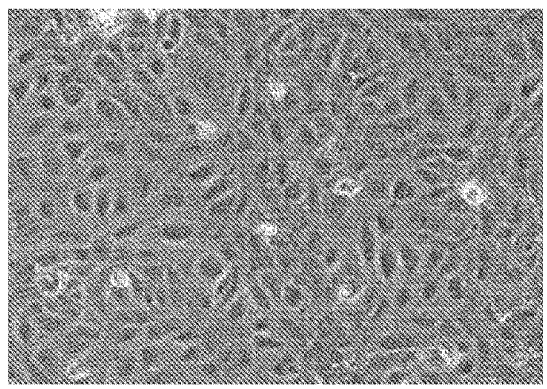
FIG. 19 is a microscopic photograph at ×100 magnification showing a cultivated state 3 days after the cultivation onto a sample having a membrane thickness of 0.2 µm of example 6.
Figure 20:
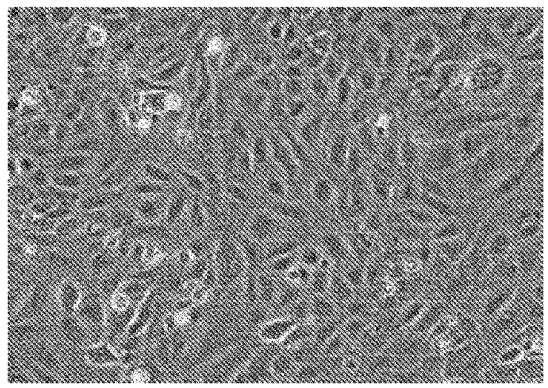
FIG. 20 is a microscopic photograph at ×100 magnification showing a cultivated state 3 days after the cultivation onto a sample having a membrane thickness of 0.3 µm of example 6.

FIG. 19 shows a cultivated state 3 days after the cultivation carried out in example 6 by using the polymer membrane having a membrane thickness of 0.2 μm. Moreover, FIG. 20 shows a cultivated state 3 days after the cultivation carried out in example 6 by using the polymer membrane having a membrane thickness of 0.3 μm.

Example 7

(Cultivation of HEK293 Cells Derived from Human Fetus Kidney)

By using the same method as that of example 1, polymer membranes respectively having membrane thicknesses of 0.2 μm and 0.3 μm were formed from monoaminomethyl (2,2)paracyclophane, and cell culture substrates were respectively formed; thus, cultivations of HEK293 cells derived from human fetus kidney were carried out. The same culture conditions and culture method as those of example 6 were used.

Figure 21:
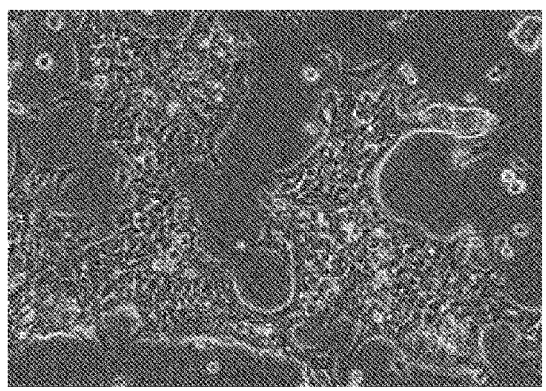
FIG. 21 is a microscopic photograph at ×100 magnification showing a cultivated state 3 days after the cultivation onto a sample having a membrane thickness of 0.2 µm of example 7.
Figure 22:
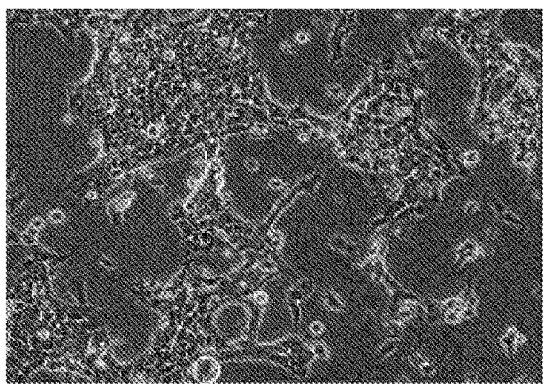
FIG. 22 is a microscopic photograph at ×100 magnification showing a cultivated state 3 days after the cultivation onto a sample having a membrane thickness of 0.3 µm of example 7.

FIG. 21 shows a cultivated state 3 days after the cultivation carried out in example 7 by using the polymer membrane having a membrane thickness of 0.2 μm. Moreover, FIG. 22 shows a cultivated state 3 days after the cultivation carried out in example 7 by using the polymer membrane having a membrane thickness of 0.3 μm.

Example 8

(Cultivation of MCF-7 Cells Derived from Human Breast Carcinoma)

By using the same method as that of example 1, polymer membranes respectively having membrane thicknesses of 0.2 μm and 0.3 μm were formed from monoaminomethyl (2,2)paracyclophane, and cell culture substrates were respectively produced; thus, cultivations of MCF-7 cells derived from human breast carcinoma were carried out. The same culture conditions and culture method as those of example 6 were used.

Figure 23:
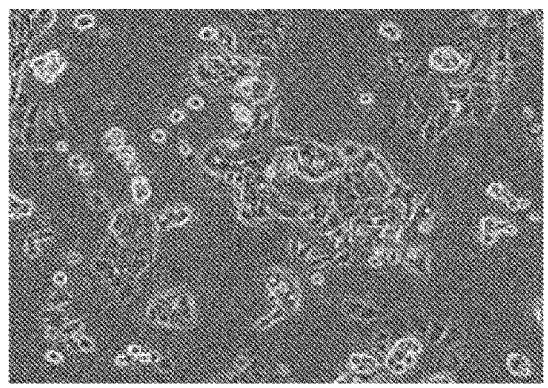
FIG. 23 is a microscopic photograph at ×100 magnification showing a cultivated state 3 days after the cultivation onto a sample having a membrane thickness of 0.2 µm of example 8.
Figure 24:
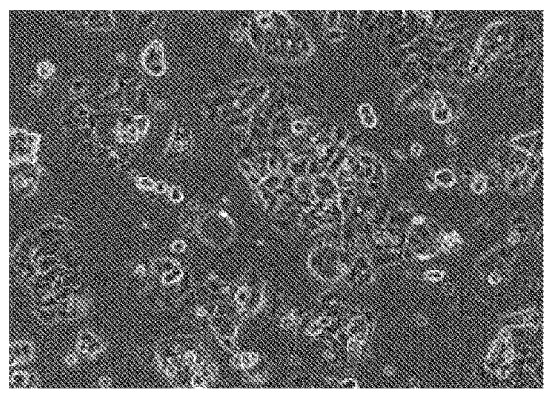
FIG. 24 is a microscopic photograph at ×100 magnification showing a cultivated state 3 days after the cultivation onto a sample having a membrane thickness of 0.3 µm of example 8.

FIG. 23 shows a cultivated state 3 days after the cultivation carried out in example 8 by using the polymer membrane having a membrane thickness of 0.2 μm. FIG. 24 shows a cultivated state 3 days after the cultivation carried out in example 8 by using the polymer membrane having a membrane thickness of 0.3 μm.

Example 9

(Cultivation of Caco-2 Cells Derived from Human Colon Cancer)

By using the same method as that of example 1, a polymer membrane having a membrane thicknesses of 0.7 μm was formed from monoaminomethyl(2,2)paracyclophane, and a cell culture substrate was produced; thus, cultivations of Caco-2 cells derived from human colon cancer were carried out. The same culture conditions and culture method as those of example 6 were used.

Figure 25:
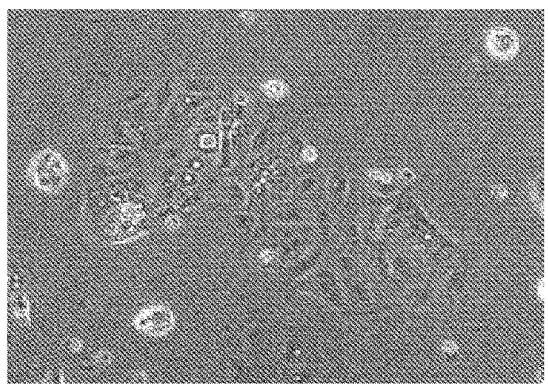
FIG. 25 is a microscopic photograph at ×100 magnification showing a cultivated state 3 days after the cultivation onto a sample having a membrane thickness of 0.7 µm of example 9.
Figure 26:
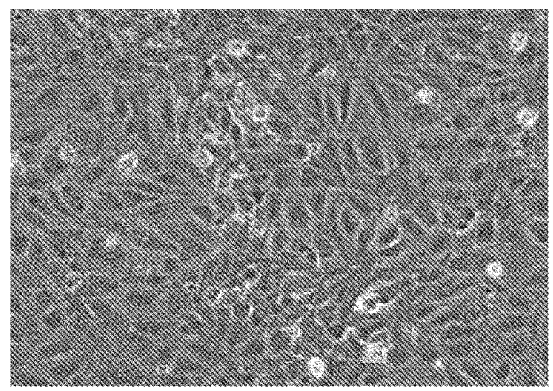
FIG. 26 is a microscopic photograph at ×100 magnification showing a cultivated state 3 days after the cultivation of HUVEC cells onto a TC processed product of comparative example 4.
Figure 27:
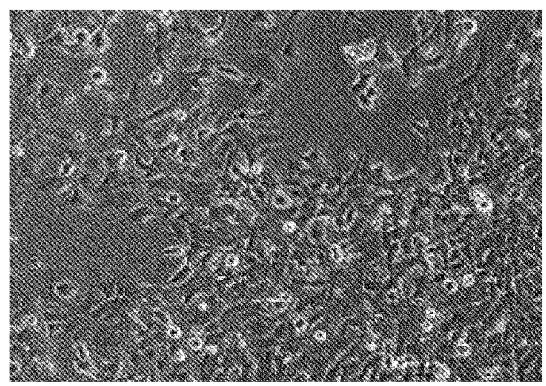
FIG. 27 is a microscopic photograph at ×100 magnification showing a cultivated state 3 days after the cultivation of HEK293 cells onto a TC processed product of comparative example 4.
Figure 28:
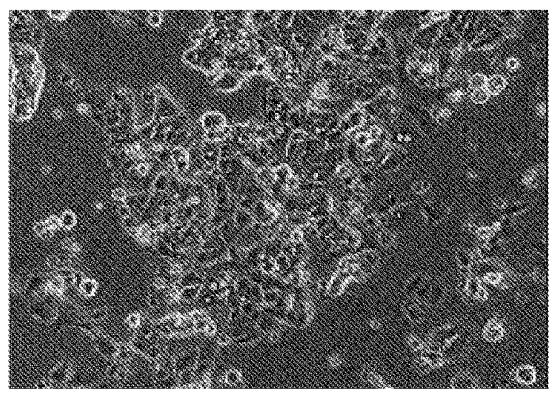
FIG. 28 is a microscopic photograph at ×100 magnification showing a cultivated state 3 days after the cultivation of MCF-7 cells onto a TC processed product of comparative example 4.
Figure 29:
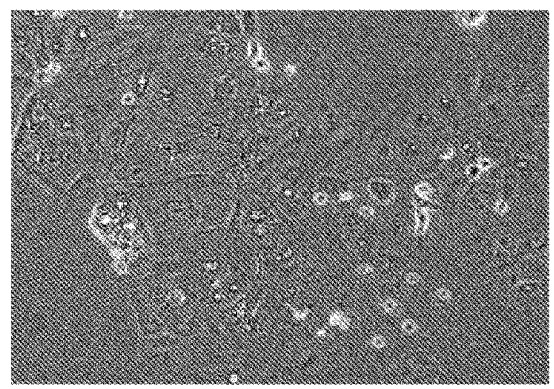
FIG. 29 is a microscopic photograph at ×100 magnification showing a cultivated state 3 days after the cultivation of Caco-2 cells onto a TC processed product of comparative example 4.
Figure 30:
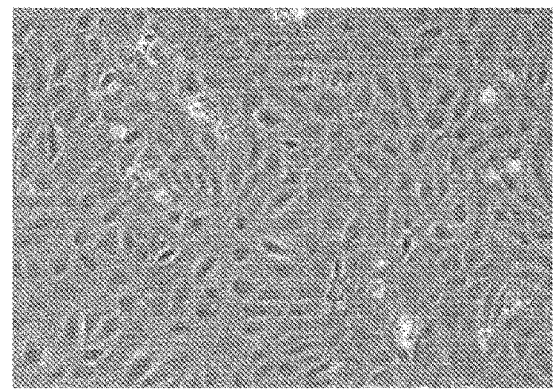
FIG. 30 is a microscopic photograph at ×100 magnification showing a cultivated state 3 days after the cultivation of HUVEC cells onto a collagen-coated product of comparative example 4.
Figure 31:
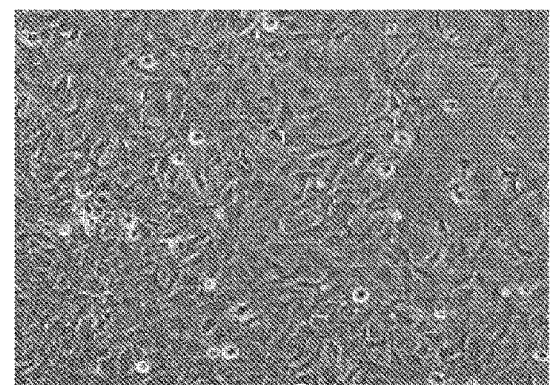
FIG. 31 is a microscopic photograph at ×100 magnification showing a cultivated state 3 days after the cultivation of HEK293 cells onto a collagen-coated product of comparative example 4.
Figure 32:
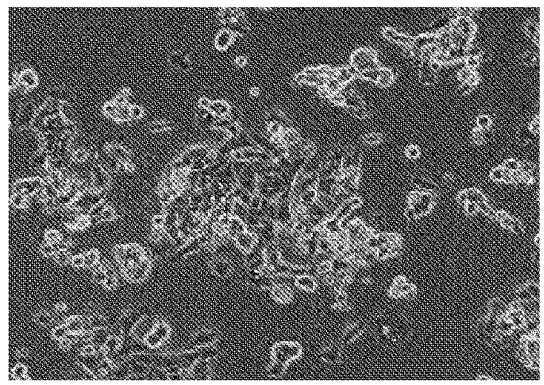
FIG. 32 is a microscopic photograph at ×100 magnification showing a cultivated state 3 days after the cultivation of MCF-7 cells onto a collagen-coated product of comparative example 4.
Figure 33:
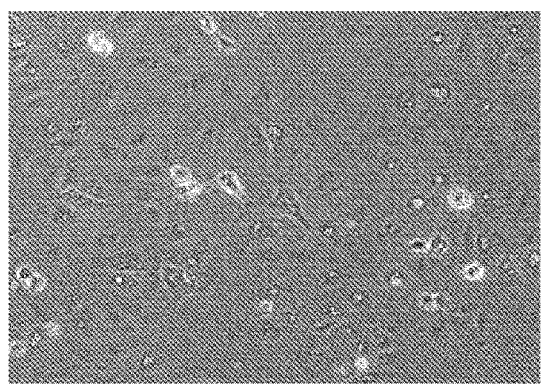
FIG. 33 is a microscopic photograph at ×100 magnification showing a cultivated state 3 days after the cultivation of Caco-2 cells onto a collagen-coated product of comparative example 4.
Figure 34:
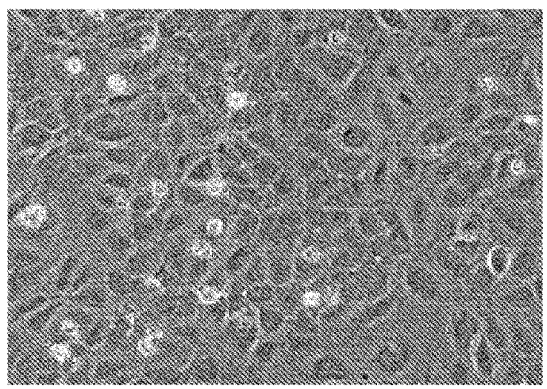
FIG. 34 is a microscopic photograph at ×100 magnification showing a cultivated state 3 days after the cultivation of HUVEC cells onto a commercially-available product of comparative example 4.
Figure 35:
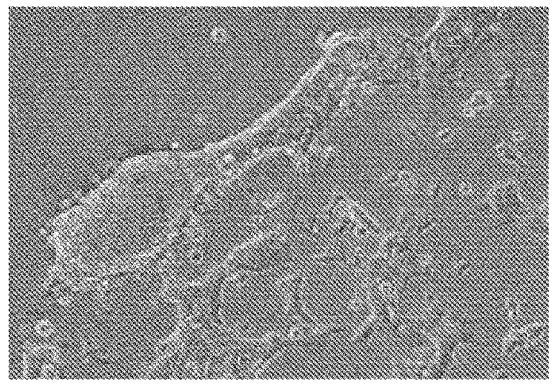
FIG. 35 is a microscopic photograph at ×100 magnification showing a cultivated state 3 days after the cultivation of HEK293 cells onto a commercially-available product of comparative example 4.
Figure 36:
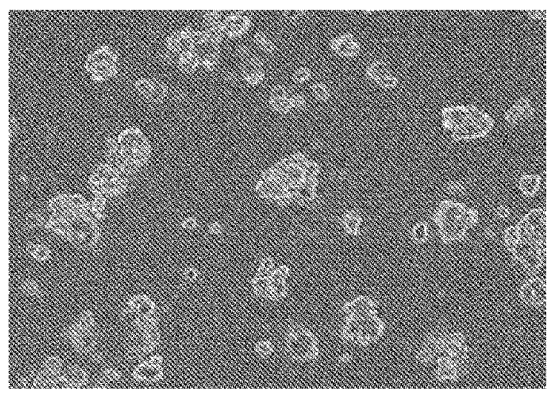
FIG. 36 is a microscopic photograph at ×100 magnification showing a cultivated state 3 days after the cultivation of MCF-7 cells onto a commercially-available product of comparative example 4.
Figure 37:
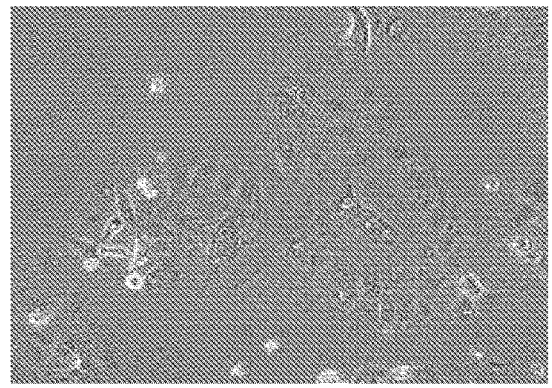
FIG. 37 is a microscopic photograph at ×100 magnification showing a cultivated state 3 days after the cultivation of Caco-2 cells onto a commercially-available product of comparative example 4.

FIG. 25 shows a cultivated state 3 days after the cultivation carried out in example 9 by using the polymer membrane having a membrane thickness of 0.7 μm.

Comparative Example 4

(Cell Cultivation by Using Generally-Used Cell Culture Substrate)

In comparative example 4, a 24 WELL cell culture multi-well plate made of polystyrene (TC processed product), which was generally used for cell cultivations, a 24 WELL cell culture multi-well plate made of polystyrene and coated with collagen, and a commercially available plate (PureCoat Amine, made by BD Company.) were used, and cultivations of the endothelial cell HUVEC of human umbilical cord vein vascular, HEK293 cells derived from human fetus kidney, MCF-7 cells derived from human breast carcinoma and Caco-2 cells derived from human colon cancer were carried out thereon by using the same methods as those of examples 6 to 9.

FIGS. 26 to 29 respectively show cultivated states of HUVEC cells, HEK293 cells, MCF-7 cells and Caco-2 cells 3 days after the cultivations carried out by using the TC processed product of comparative example 4. FIGS. 30 to 33 respectively show cultivated states of HUVEC cells, HEK293 cells, MCF-7 cells and Caco-2 cells 3 days after the cultivations carried out by using the collagen-coated product of comparative example 4. Moreover, FIGS. 34 to 37 respectively show cultivated states of HUVEC cells, HEK293 cells, MCF-7 cells and Caco-2 cells 3 days after the cultivations carried out by using a commercially available product.

Table 4 shows the results of cultivations of the various cells that were carried out in examples 6 to 9, and Table 5 shows the results of cultivations of the various cells that were carried out in comparative example 4. Additionally, the examination results of adhesion properties shown in Table 4 and Table 5 are results obtained on the $5^{th}$ day after the cultivations, and "◯" indicates that cell adhesion capability was obtained, while and "X" indicates that no cell adhesion capability was obtained. Moreover, "-" indicates conditions where no tests were carried out.

TABLE 4

| Cell adhesion layer | | Copolymer of monoaminomethylparaxylylene and paraxylylene | | |
|---|---|---|---|---|
| Membrane thickness | | 0.2 μm | 0.3 μm | 0.7 μm |
| Example 6 | HUVEC | ◯ | ◯ | — |
| Example 7 | HEK293 | ◯ | ◯ | — |
| Example 8 | MCF-7 | ◯ | ◯ | — |
| Example 9 | Caco-2 | — | — | ◯ |

TABLE 5

| | | Comparative Example 4 | |
|---|---|---|---|
| Cell adhesion layer | TC processed product | Collagen coat | PureCoat Amine made by BD Company |
| HUVEC | ◯ | ◯ | ◯ |
| HEK293 | ◯ | ◯ | X |
| MCF-7 | ◯ | ◯ | X |
| Caco-2 | ◯ | ◯ | ◯ |

As clearly indicated by the cultivation results shown in Table 4 and Table 5, although the HUVEC and Caco-2 cells were adhered to any of the plates, HEK293 cells and MCF-7 cells were not adhered to the PureCoat Amine made by BD Company. used in comparative example 4. In contrast, in the cell culture substrates used in examples 6 to 9, all the cells were adhered thereto, providing a good cell adhesion capability. These facts indicate, that the cell culture substrates used in examples 6 to 9 had no cell type dependency.

<Micro-Array Analysis of Cultivated HepG2 Cells Derived from Human Hepatic Cancer>

Example 10

By using the same method as that of example 1, polymer membranes respectively having membrane thicknesses of 0.5 μm was formed from monoaminomethyl(2,2)paracyclophane, and a cell culture substrate was produced; thus, cultivation of HepG2 cells was carried out by using the same method as that of example 5. Next, from the cultivated HepG2 cells, all the RNA's were extracted and refined by using RNeasy Mini Kit (QIAGEN), and all the RNA's were sent to Takara Bio Inc. to entrust them to carry out micro-array analyses thereon. Thereafter, the resulting analyzed data were quality-managed and genes that were increased two or more times as many as those at the time of cultivation by using a normal TC treated plate were extracted and subjected to a cluster-analysis by using a Cluster 3. Moreover, in order to carry out a visualizing process, a Java TreeView was used.

Comparative Example 5

(Micro-Array Analysis Upon Cultivation of HepG2 Cells Derived from Human Hepatic Cancer by Generally-Used Cell Culture Substrate)

In comparative example 5, a 24 WELL cell culture multi-well plate made of polystyrene (TC processed product), which was generally used for cell cultivations, a 24 WELL cell culture multi-well plate made of polystyrene and coated with collagen, and a commercially available product (PureCoat Amine, made by BD Company.) were used, and HepG2 cells were cultivated by using the same method as that of example 10, and subjected to a micro-array analysis.

Figure 38:
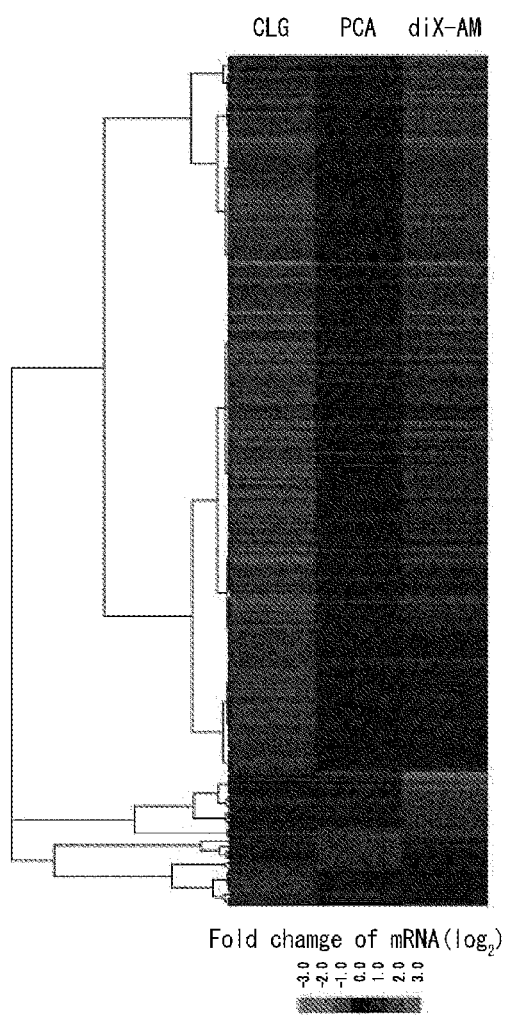
FIG. 38 shows results of cluster analysis corresponding to the results of micro-array analysis of example 10 and comparative example 5.

FIG. 38 shows the results of the micro-array analysis of the HepG2 cells derived from human hepatic cancer cultivated in example 10 and comparative example 5.

As clearly indicated by FIG. 38, it is found, as a result of the cluster analysis, that patterns of genes developed and raised were resemble to each other between those cultivated with the polymer membrane obtained from monoaminomethyl(2,2)paracyclophane and those cultivated with the collagen-coated plate. In contrast, in the case of those cultivated by using the PureCoat Amine, there were not so many fluctuations in genes as a whole, and they were found to be different from those cultivated with the collagen-coated plate.

REFERENCE SIGNS LIST

11 . . . evaporation unit, 11a . . . vapor deposition material loading inlet, 12 . . . decomposition unit, 13 . . . vapor deposition unit, 14 . . . trap, 15 . . . vacuum pump

The invention claimed is:
1. A cell culture substrate comprising:
 a polymer membrane, comprising a structural unit represented by the following formula (I) and formed on a base,

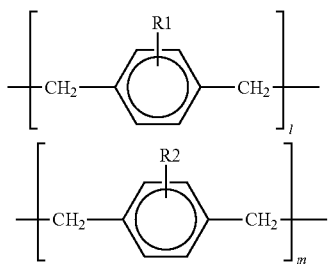

(I)

(in the formula, R1 and R2 represent a direct —($CH_2$)$_n$—$NH_2$ moiety (n is an integer of 1-10 inclusive) or H, with at least one of R1 and R2 in all of the structural units in the polymer being a direct —($CH_2$)$_n$—NH2 moiety, wherein 1 and m are positive integers expressing polymerization degree and wherein said membrane has a thickness of at least 0.2 μm.

2. The cell culture substrate of claim 1, wherein n is 1.

3. The cell culture substrate of claim 1, wherein said membrane has a thickness of 0.2 μm.

4. The cell culture substrate of claim 1, wherein said membrane has a thickness of 0.3 μm.

5. The cell culture substrate of claim 1, wherein said membrane has a thickness of 0.7 μm.

6. The cell culture substrate of claim 1, wherein said membrane has a thickness of 1.0 μm.

7. The cell culture substrate of claim 1, wherein said membrane has a thickness of 1.1 μm.

8. The cell culture substrate of claim 1, wherein said membrane has a thickness of between 0.2 μm and 1.1 μm.

9. The cell culture substrate of claim 2, wherein said membrane has a thickness of between 0.2 μm and 1.1 μm.

10. The cell culture substrate of claim 1, wherein said base is polystyrene.

11. The cell culture substrate of claim 1, wherein said polymer membrane is a copolymer consisting of monoaminomethylparaxylylene and paraxylylene.

* * * * *